United States Patent [19]

Estreicher

[11] Patent Number: 4,564,383

[45] Date of Patent: Jan. 14, 1986

[54] USE OF 4-(HYDROXYIMINOMETHYL)CINNOLINE AND CONGENERS THEREOF FOR CONTROLLING THE GROWTH OF UNWANTED PLANTS

[75] Inventor: Herbert Estreicher, Modesto, Calif.

[73] Assignee: Shell Oil Company, Houston, Tex.

[21] Appl. No.: 523,228

[22] Filed: Aug. 15, 1983

[51] Int. Cl.$^4$ .............................................. A01N 43/58
[52] U.S. Cl. ........................................................ 71/92
[58] Field of Search ............................................ 71/92

[56] References Cited

U.S. PATENT DOCUMENTS

| | | | |
|---|---|---|---|
| 3,657,241 | 4/1972 | Kurihara | 71/92 X |
| 3,749,718 | 7/1973 | Ailman | 71/92 X |
| 4,229,205 | 10/1980 | Theobald et al. | 71/92 |

OTHER PUBLICATIONS

Castle et al., J. Org. Chem. vol. 26 (1961), 4465–4469.

*Primary Examiner*—Catherine L. Mills

[57] ABSTRACT

The growth of unwanted plants is controlled by 4-(hydroxyiminomethyl)cinnoline and congeners thereof.

1 Claim, No Drawings

USE OF 4-(HYDROXYIMINOMETHYL)CINNOLINE AND CONGENERS THEREOF FOR CONTROLLING THE GROWTH OF UNWANTED PLANTS

DESCRIPTION OF THE INVENTION

It has been found that the growth of certain plants is adversely affected by 4-(hydroxyiminomethyl)cinnoline and certain of its congeners, of the formula:

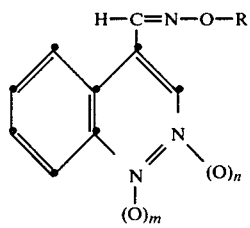

wherein m is zero or one, n is zero or one, R is hydrogen, or optionally substituted alkyl of up to ten carbon atoms, and salts of the compound wherein R is hydrogen.

In these compounds, the alkyl moiety may be either straight-chain or branched-chain in configuration. Suitable substituents in the alkyl moiety include one or more halogen atoms (bromine, chlorine or fluorine being preferred), alkoxy, alkylthio, alkanoyl, alkanoyloxy, carboxyl, alkyloxycarbonyl, aminocarbonyl, alkylthiocarbonyl, alkenyl, alkynyl, cycloalkyl of from three to six carbon atoms and optionally substituted phenyl, with the proviso that in the cases of the halogen, alkoxy, alkylthio and alkanoxyloxy moieties, the substituent is bonded to a carbon atom of the alkyl moiety other than the carbon atom thereof that is bonded to the oxygen atom of the oximino moiety. Suitable substituents on the phenyl moiety include halogen, mono- and polyhaloalkyl, cyano, carboxyl, nitro, amino, mono- and dialkylamino, alkylsulfonamido, alkylsulfonyl, alkoxycarbonyl, alkylaminosulfonyl, alkyl, alkoxy and alkylthio. In these substituent moieties, each alkyl moiety suitably contains from one to four carbon atoms, and is either straight-chain or branched-chain in configuration.

The contemplated salts are hydrohalide salts and the salts of alkali metals, alkaline earth metals, amines and ammonia. Suitable amine salts are those of mono-, di-, and tri-alkyl- and alkanol-amines wherein each alkyl moiety contains up to twenty carbon atoms.

Compounds of Formula I can exist in the form of geometrical isomers, referring to the spatial relationship of the moieties about the oxime double bond. In the cases of the compounds whose preparation and isolation as described in the working examples, hereinafter, the geometric form(s) of the products has not been determined, and no attempt has been made to resolve the isomeric compounds involved. The activities of the isomers with respect to plants may differ. This invention contemplates all active isomers, and mixtures thereof, whether resulting from the manner of preparation or deliberately formed.

4-(hydroxyiminomethyl)cinnoline is a known compound; Castle, R. N. and Onda, M., *J. Org. Chem.*, 1961, 26, 4465-4469.

As is shown in the Examples, hereinafter, the congener ethers (R=optionally substituted alkyl) can be prepared by treating a mixture of the oxime and potassium carbonate in methanol with the appropriate R-halide. The oxides are readily prepared by conventional oxidation of the cinnoline (m is zero; n is zero) precursor using meta-chloroperoxybenzoic acid, or similar oxidizing agent. The oxidation is conveniently effected by slowly adding an excess of the oxidizing agent to a solution of the cinnoline in an inert solvent such as methylene dichloride at a low temperature (for example, about 0° C.), maintaining the cold mixture for a time sufficient for the reaction to go to completion, decomposing excess oxidizing agent, using sodium sulfite or sodium thiosulfate, then isolating the oxides, using conventional work-up techniques.

The following examples describe the preparation, isolation and physical properties of typical individual species of the compounds of Formula I, in particular instances. In each case, the identity of each product, and each of any intermediate involved, was confirmed by appropriate chemical and spectral analyses.

EXAMPLE 1

4-(hydroxyiminomethyl)cinnoline hydrochloride (1) and 4-(hydroxyiminomethyl)cinnoline (2)

A solution of 50.0 g of o-isopropenylaniline (Aldrich) in 440 ml of 2N hydrochloric acid was treated with 86 ml of 12N hydrochloric acid at 20° C. The resulting mixture was extracted with ether to remove a small amount of an insoluble oil. The aqueous phase was cooled to 0° C. and treated with 24.5 g of sodium nitrite, in portions, over 2 hours, at 0°-5° C. The resulting mixture was stirred for 30 minutes at 0° C., warmed to room temperature, heated to 60° C., held at room temperature over a weekend, neutralized with sodium bicarbonate, made basic with 50% sodium hydroxide solution, and extracted with ether. The extract was washed with brine, dried (MgSO4), charcoaled, filtered and stripped of solvent. The residue was recrystallized from hexane to give 4-methylcinnoline (1A), as a solid, m.p.: 70°-72° C.

A solution of 1.44 g of 1A in 3 ml of absolute ethanol was aded over 3 minutes to 3.4 ml of stirred ethanol containing 0.9 g of anhydrous hydrogen chloride, at 0° C. The resulting mixture was stirred for 30 minutes, then a solution of 1.03 g of butyl nitrite in 2 ml of absolute ethanol was added drop-by-drop over 3 minutes at 0° C. The mixture was stirred for 30 minutes at 0° C., then for 4 hours at room temperature, then stored in a refrigerator overnight. A precipitated solid was filtered, washed with a small amount of water, and dried to give 1, as a yellow solid, m.p.: 210° C. (with decomposition).

0.95 g of 1 was mixed with saturated aqueous potassium bicarbonate solution. The resulting solid was filtered and recrystallized from water to give 2, as a solid, m.p.: 223° C. (with decomposition).

EXAMPLE 2

Sodium salt (3) of 2

A slurry of 0.52 g of 2 in 15 ml of dry methanol was added, at 20° C., to 0.069 g of sodium metal dissolved in 3 ml of dry methanol. The resulting mixture was stirred at room temperature overnight, the solvent was evaporated and the residue was triturated with ether to give 3, as a solid, m.p.: 224°-226° C. (with decomposition).

EXAMPLE 3

4-(methoxyiminomethyl)cinnoline (4)

A suspension of 463 mg of 2 and 370 mg of potassium carbonate in 40 ml of dry methanol was heated at 40° C. until the mixture became homogeneous (1 hour). Then 2.0 ml of methyl iodide was added and the mixture was held at 40° C. for 6 hours, then at room temperature overnight. Then the solvent was evaporated and the residue was flash chromatographed on silica gel, using 2:3 v:v mixture of ethyl acetate and methylene chloride as eluent. Workup gave 4, as a yellow solid, m.p.: 83°–85° C.

EXAMPLE 4

4-(ethoxyiminomethyl)cinnoline (5)

A stirred suspension of 1.0 g of 2 and 0.8 g of potassium carbonate in 40 ml of dry methanol was held at room temperature for 3 hours. Then 0.47 g of ethyl iodide was added and the resulting mixture was held for 18 hours at room temperature in an aluminum foil-covered flask. Then the solvent was evaporated under reduced pressure, the residue was dissolved in ether, and the resulting mixture was filtered. The solvent was evaporated from the filtrate and the residue was chromatographed on silica gel, using a 1:2 v:v mixture of ethyl acetate and hexane as eluent, to give 5, as a yellow solid, m.p.: 78°–81° C.

EXAMPLES 5–7

By the procedures described in Example 4, 4-(propoxymethyl)cinnoline (6) was prepared as a solid, m.p.: 50°–54° C., from propyl iodide, 4-(butoxyiminomethyl)cinnoline (7) was prepared, as a solid, m.p.: 48° C., from butyl iodide, and 4-(allyloxyiminomethyl)cinnoline (8) was prepared, as a yellow solid, m.p.: 67°–70° C., from allyl bromide.

Compounds of Formula I have been found to adversely affect the growth of some plants, many of which are commonly considered as weeds, and therefore to be useful for controlling the growth of such unwanted plants. Compounds of Formula I have been found to have selectivity with respect to some crop plants—i.e., they control weeds at dosages at which they do not significantly harm the crop plants. While compounds of Formula I appear to have some activity when applied preemergence or preplant incorporated (applied to the soil before the seeds have sprouted), most appear to be more effective when applied post-emergence (applied to the foliage of the growing plant).

Accordingly, the invention includes a method of combatting unwanted plants which comprises applying to the locus an effective amount of a compound of Formula I. In the cases where it is desired to control weeds in crop plantings, it is of course preferable to employ the lowest dosage that will control the weeds, for this will minimize any possible deleterious effect of the compound upon the crop plants. For application, the compound generally is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or fluid material, which may be inorganic or organic and of synthetic or natural origin, with which the active compound is mixed or formulated to facilitate its application to the plant, seed soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or alophatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compounds and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:

Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*

TEST PROCEDURES

The preemergence (soil) herbicidal activity of the compounds was evaluated by planting seeds of barnyardgrass, garden cress, downy bome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of the invention was evaluated by spraying 10-day-old large downy brome plants in some cases, 6-day-old Johnsongrass plants in other cases, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence herbicidal activity tests are set forth in Table I.

TABLE I
HERBICIDAL ACTIVITY

| Compound | Preemergence | | | | | | Postemergence | | | | | |
|---|---|---|---|---|---|---|---|---|---|---|---|---|
| | Barnyard-grass | Garden Cress | Downy Brome | Velvet-leaf | Yellow Foxtail | Sickle-pod | Crab-grass | Pig-weed | Johnson-grass | Velvet-leaf | Yellow Foxtail | Sickle-pod |
| 1 | 3 | 4 | 0 | 0 | 8 | 0 | 6 | 0 | 3 | 2 | 9 | 0 |
| 2 | 3 | 6 | 2 | 0 | 9 | 3 | 6 | 2 | 2 | 2 | 9 | 2 |
| 3 | 0 | 0 | 0 | 0 | 4 | 0 | 7 | 2 | 0 | 0 | 8 | 0 |
| 4 | 0 | 5 | 0 | 0 | 0 | 0 | 6 | 4 | 2 | 2 | 9 | 2 |
| 5 | 0 | 0 | 0 | 0 | 0 | 0 | 7 | 3 | 1 | 2 | 9 | 2 |
| 6 | 0 | 0 | 0 | 0 | 0 | 0 | 9 | 6 | 1 | 2 | 7 | 2 |
| 7 | 2 | 3 | 0 | 0 | 0 | 0 | 8 | 9 | 1 | 2 | 8 | 2 |
| 8 | 0 | 0 | 0 | 0 | 0 | 0 | 7 | 6 | 1 | 2 | 7 | 2 |

EXAMPLES OF SELECTIVITY

In the following examples, the species of plants that were tested were:

Barnyardgrass
Downy brome
Johnsongrass
Wild oats—*Avena fatua*
Yellow foxtail
Goose grass—*Eleusine indica* L.
Yellow nutsedge—*Cyperus esculentus* L.
Cocklebur—*Xanthum pennsylvanicum*
Morningglory—*Ipomoea purpurea* L. (Roth)
Wild mustard—*Brassica kaber*
Redroot pigweed
Sicklepod
Velvetleaf
Corn—*Zea mays*
Cotton—*Gossypium hirsutum*
Rice—*Oryza sativa*
Grain sorghum—*Sorghum vulgare*
Soybeans—*Glycine max*
Sugarbeets—*Beta vulgaris*
Wheat—*Triticum aestivum*

TEST PROCEDURES

The preemergence activity of compounds of Formula I was further determined with respect to certain species of crop plants and common species of weeds, by spraying a formulation of the test compound on soil in small pots in which seeds of the plants had been sown. The postemergence herbicidal activity of compounds of Formula I was evaluated with respect to the crop plants and weeds, by spraying a formulation of the test compound on the foliage of the young growing plants. In each series of tests, the plants were grown in narrow trays and sprayed with the formulation. Dosages of the test compounds of 2.0 pounds/acre in some cases, and 1.0 or 0.25 pound/acre in all cases, were used. The results of the tests were evaluated on the basis of the 0–9 scale described with respect to the earlier tests. Activity of the test compound in such case was characterized as follows:

| | Dosage (lb/acre) | Rating (one or another) |
|---|---|---|
| Highly active | 0.25 | 8–9 |
| | 1.0 | 8–9 |
| | 2.0 | 8–9 |
| Very active | 0.25 | 6–7 |
| | 1.0 | 8–9 |
| | 2.0 | 8–9 |
| Active | 0.25 | 4–5 |
| | 1.0 | 6–7 |
| | 2.0 | 7–9 |
| Slightly active | 0.25 | 2–3 |
| | 1.0 | 3–4 |
| | 2.0 | 4–5 |
| Essentially inactive | 0.25 | 0–1 |
| | 1.0 | 0–3 |
| | 2.0 | 1–3 |

Compounds 1 and 2 were tested preemergence: Compound 1 was very active with respect to yellow foxtail and essentially inactive with respect to all of the varieties of test plants. Compound 2 was essentially inactive with respect to all of the varieties of test plants.

All of Compounds 1 through 8 were tested postemergence.

With respect to yellow foxtail, Compounds 4 and 8 were highly active; Compounds 5–7 were very active; Compounds 2 and 3 were active; and Compound 1 was slightly active.

With respect to cocklebur, Compounds 5 and 6 were slightly active; and Compounds 1–4, 7 and 8 were essentially inactive.

With respect to morningglory, Compounds 5, 6 and 7 were slightly active; and Compounds 1–4 and 8 were essentially inactive.

With respect to all of the other varieties of plants, all of the compounds were essentially inactive.

I claim:

1. A method for controlling the growth of unwanted plants, which method comprises applying to the foliage of the plants an effective amount of a compound of the formula

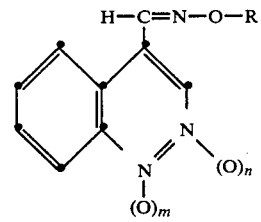

(I)

wherein m is zero or one, n is zero or one, R is hydrogen, or contains from one to ten carbon atoms and is alkyl optionally substituted by alkenyl, and salts of the compounds wherein R is hydrogen.

* * * * *